United States Patent [19]

Rajagopalan et al.

[11] Patent Number: 5,656,253
[45] Date of Patent: Aug. 12, 1997

[54] LIGANDS USEFUL IN RADIOGRAPHIC IMAGING

[75] Inventors: Raghavan Rajagopalan, Maryland Heights; Ananthachari Srinivasan, St. Charles; Jean-Luc Vanderheyden, St. Louis, all of Mo.

[73] Assignee: Mallinckrodt Medical, Inc., St. Louis, Mo.

[21] Appl. No.: 255,148

[22] Filed: Jun. 7, 1994

Related U.S. Application Data

[63] Continuation-in-part of Ser. No. 13,527, Feb. 4, 1993, abandoned, which is a continuation-in-part of Ser. No. 831,724, Feb. 5, 1992, Pat. No. 5,382,654, Ser. No. 842,017, Feb. 25, 1992, abandoned, and Ser. No. 183,270, Jan. 19, 1994, abandoned, which is a continuation of Ser. No. 584,317, Sep. 14, 1990, abandoned.

[51] Int. Cl.⁶ .................. A61K 51/00; A61K 7/32; C07D 401/02; C07D 211/70
[52] U.S. Cl. .................. 424/1.11; 424/1.65; 546/334; 546/336; 546/278.7; 546/282.1; 546/282.4; 546/283.4; 546/283.7
[58] Field of Search .................. 424/1.11, 1.65; 534/10, 14; 546/2.68, 334, 336, 283

[56] References Cited

U.S. PATENT DOCUMENTS

| | | | |
|---|---|---|---|
| 4,577,042 | 3/1986 | Collins et al. | 564/158 |
| 4,965,392 | 10/1990 | Fritzberg et al. | 558/254 |
| 4,988,496 | 1/1991 | Srinivasan et al. | 424/1.11 |
| 5,202,451 | 4/1993 | Fritzberg et al. | 556/419 |
| 5,310,536 | 5/1994 | Srinivasan | 424/1.65 |
| 5,371,184 | 12/1994 | Rajagopalan et al. | 530/324 |
| 5,382,654 | 1/1995 | Lyle et al. | 530/311 |

FOREIGN PATENT DOCUMENTS

| | | |
|---|---|---|
| 0200211 | 11/1986 | European Pat. Off. . |
| 9205154 | 4/1992 | WIPO .................. A61K 49/02 |

OTHER PUBLICATIONS

McOmie, "Protective Groups in Organic Chemistry", pp. 235–238, Plenium Press; (1973).

Hackh's "Chemical Dictionary", pp. 148, 388 (1983).

Lundeen, et al., "Sulfinato Coordination of Triplet–State . . . ". Inorg. Chem. 17(3), pp. 701–706 (1978).

Mueller, et al., "Pyridlalkyl amides", Chemical Abstract 105:226378c (1986).

Lomis, et al., "Effects of a thio group . . . ", Chemical Abstract 111:107960a (1986).

Fuller, "Acyclaminoalkylpyridineamides . . . ", Chemical Abstract 114:75196z (1986).

Handa, et al., "Synthesis, Properties . . . ", Chemical Abstract 110:87409b (1989).

Bryson, et al., "Protecting Groups in the preparation of thiolate complexes of Technetium", p. 2950, Inorg. Chem., vol. 29, No. 16 (1990).

McKenzie, "Complexes of binucleating ligands", p. 5616, Inorg. Chem., vol. 26, No. 21 (1987).

*Primary Examiner*—Shean C. Wu
*Attorney, Agent, or Firm*—Wendell Ray Guffey; Thomas P. McBride

[57] ABSTRACT

The present invention relates particularly to novel pyridine based nitrogen-sulfur ligands that are suitable for complexing with a radionuclide, and are useful as general imaging agents for diagnostic purposes, novel aminothiol ligands that are suitable for complexing with a radionuclide, and are useful as general imaging agents for diagnostic purposes, and amide-thiolate ligands having improved metal chelate formation kinetics. The amide-thiolate ligands include an amine which converts to a vinylogous amide upon complexation, thereby providing rapid complexation and thermodynamic stability. The ligands may be used for post formed labeling of biological substances for use in the fields of diagnosis and therapy.

1 Claim, No Drawings

LIGANDS USEFUL IN RADIOGRAPHIC IMAGING

This is a Continuation-In-Part Application of U.S. Ser. No. 08/013,527, filed Feb. 4, 1993, now abandoned, which is a Continuation-In-Part application of U.S. Ser. No. 07/831,724, filed Feb. 5, 1992, now U.S. Pat. No. 5,382,654, Ser. No. 07/842,017 filed Feb. 25, 1992, now abandoned; and U.S. application Ser. No. 08/183,270, filed Jan. 19, 1994, now abandoned, which is a Continuation of U.S. application Ser. No. 07/584,317, filed Sep. 14, 1990, now abandoned. The entirety of each of these applications is incorporated herein by reference hereto.

FIELD OF THE INVENTION

The present invention relates to novel ligands for forming radionuclide complexes, new complexes incorporating such ligands, processes for preparing such complexes, imaging agents incorporating such complexes, and methods of imaging using such imaging agents.

BACKGROUND OF THE INVENTION

Scintigraphic imaging and similar radiographic techniques for visualizing tissues in vivo are finding ever-increasing application in biological and medical research and in diagnostic and therapeutic procedures. Generally, scintigraphic procedures involve the preparation of radioactive agents which upon introduction to a biological subject, becomes localized in the specific organ, tissue or skeletal structure of choice. When so localized, traces, plots or scintiphotos depicting the in vivo distribution of radiographic material can be made by various radiation detectors, e.g., traversing scanners and scintillation cameras. The distribution and corresponding relative intensity of the detected radioactive material not only indicates the space occupied by the targeted tissue, but also indicates a presence of receptors, antigens, aberrations, pathological conditions, and the like.

In general, depending on the type of radionuclide and the target organ or tissue of interest, the compositions comprise a radionuclide, a carrier agent designed to target the specific organ or tissue site, various auxiliary agents which affix the radionuclide to the carrier, water or other delivery vehicles suitable for injection into, or aspiration by, the patient, such as physiological buffers, salts, and the like. The carrier agent attaches or complexes the radionuclide to the carrier agent, which results in localizing the radionuclide being deposited in the location where the carrier agent concentrates in the biological subject.

Triamidethiolate and diamidedithiolate ligands have been used successfully for radiolabeling macromolecules. In general, amide-thiolate systems require harsh (75° C.–100° C.) radiolabeling conditions for preparing Tc and Re complexes. Under these conditions, the stability and biological properties of the small and medium bioactive peptides are often degraded.

In order to avoid harsh labeling conditions, pre-formed complexes have been coupled to the protein with some success. See Fritzberg et al., U.S. Pat. Nos. 4,965,392 and 5,037,630 incorporated herein by reference. In the "pre-formed approach," the ligand is complexed with the radionuclide and then conjugated to the bioactive peptide. A major disadvantage of the pre-formed approach is that the end user must perform both the radiolabeling step and the coupling step (attaching the complex to the bioactive peptide). The final product must be purified prior to administration. In the case of small and medium sized peptides, the metal-complex may potentially react with "active sites" of the peptide. Thus, site specific attachment of a ligand to a bioactive molecule is only possible with post-formed complexes.

In the conventional "post-formed approach," the ligand is first conjugated to the peptide and the resulting conjugate is labeled with the radioisotope under complex forming conditions. In the present invention, the post-formed approach has the additional advantage of allowing preparation of the conjugated bioactive peptide in kit form. The end users would perform only the radiolabeling step.

It has been found that the presence of free thiol (instead of protected thiol) and/or replacement of an amide with an amine causes labeling of $N_2S_2$ and $N_3S$ ligands to proceed under milder conditions, but at the expense of some complex stability. See Rao et al., "Tc-Complexation of $N_2S_2$ Monoaminemonoamides," *Int. J. Radiat. Part B*, (1991) (in press). In addition, Misra et al., "Synthesis of a Novel Diaminodithiol Ligand for Labeling Proteins and Small Molecules with Technetium-99 m," *Tetrahedron Letters*, Vol. 30, No. 15, pp. 1885–88 (1989) and Baidoo et al., "Synthesis of a Diaminedithiol Bifunctional Chelating Agent for Incorporation of Technetium-99 m into Biomolecules," *Bioconjugate Chemistry*, Vol. 1, pp. 132–37 (1990), report that diaminedithiol (DADT) ligands label with $^{99m}Tc$ at ambient temperatures.

Gustavson et al., "Synthesis of a New Class of Tc Chelating Agents: $N_2S_2$ Monoaminemonoamide (MAMA) Ligands," *Tetrahedron Letters*, Vol. 32, No. 40, pp. 5485–88 (1991), compares the radiolabeling efficiency of a $N_2S_2$-diamidedithiol (DADS) ligand with a $N_2S_2$-monoamine amide (MAMA) ligand. It was found that substitution of the amide nitrogen in the DADS ligand with an amine nitrogen in the MAMA ligand produced a threefold increase in radiochemical yield when labeling with $^{99m}Tc$ at 37° C. for 30 minutes.

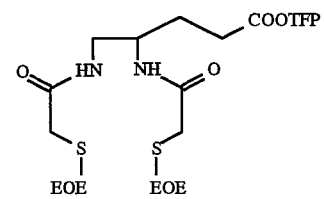

DADS

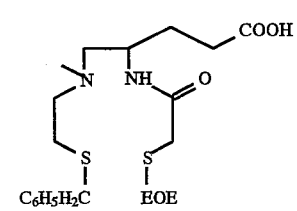

MAMA

Notwithstanding the improved metal complex formation kinetics reported with amine-containing $N_2S_2$ and $N_3S$ ligands, Tc and Re amide-thiolate complexes assure maximum in vivo stability and inhibit metal oxidation to the pertechnetate or perrhenate oxidation state.

From the foregoing, what is needed in the art are novel ligands for forming radionuclide complexes, complexes incorporating such ligands, processes for preparing such complexes, imaging agents incorporating such complexes, methods of imaging using such imaging agents, and, in particular, an amide-thiolate ligand with improved complex formation kinetics which can be labeled under mild conditions and which has excellent in vivo complex stability.

SUMMARY OF THE INVENTION

The present invention is directed to novel aminothiol ligands that are suitable for complexing with a radionuclide and which are useful as general imaging agents for diagnostic purposes and novel amide-thiolate ligands having improved complex formation kinetics. The present invention also includes radiolabeled peptide compounds utilizing the disclosed ligands, methods of preparing these compounds, pharmaceutical compositions comprising these compounds and the use of these compounds in kits for therapeutic and diagnostic applications.

The $N_3S$ amide-thiolate ligands according to the present invention contain an amine within the $N_3S$ core, to enhance initial complex formation kinetics, which converts to a thermodynamically stable amide during complex formation. Metal chelate complex formation occurs under mild conditions which do not adversely affect the targeting ability or biological activity of the carrier molecule. For most purposes, a complexing temperature in the range from about 25° C. to about 50° C. and a pH in the range from about 3–8 are sufficiently mild for small and medium peptides.

The amide-thiolate and aminothiol ligands within the scope of the present invention can be coupled as conjugates with biologically active molecules or biomolecules that are known to concentrate in the organ or tissues to be examined. These biomolecules include, for example, growth factors and synthetic analogs such as somatostatin, hormones such as insulin, prostaglandins, steroid hormones, amino sugars, peptides, proteins, lipids, conjugates with albumins, such as human serum albumin, antibodies, monoclonal antibodies specific to tumor associated antigens, or antimycin, and the like. The diagnostic media formed therefrom may be used in diagnostic and therapeutic applications.

In the present invention, the amide-thiolate and/or amino thiol ligand is coupled to a biomolecule according to standard procedures known in the art. In the case of small to medium peptides, the active sites of the biomolecules are protected so that the ligand is specifically attached to functional groups that are not involved in binding the biomolecules to the target receptor.

The ligands and biomolecule conjugates described above are useful in diagnostic and radiotherapy applications. The compounds of the present invention may be labeled with any suitable radionuclide favorable for these purposes. Such suitable radionuclides for radiotherapy include but are not limited to $^{186}Re$, $^{188}Re$, $^{67}Cu$, $^{90}Y$, and $^{60}Co$. For diagnostic purposes the most suitable radionuclides include, but are not limited to, the transition metals as exemplified by $^{99m}Tc$, $^{111}In$, and $^{62}Cu$.

It is therefore an object of the present invention to provide amide-thiolate ligands having improved complex formation kinetics which can be labeled under mild conditions and which have excellent complex stability and aminothiol ligands suitable for use as a radionuclide when complexed with a suitable metal.

DETAILED DESCRIPTION OF THE INVENTION

The present invention relates, in one significant aspect, to novel aminothiol ligands that are suitable for complexing with a radionuclide and which are useful as general imaging agents for diagnostic purposes. In particular the present invention relates to novel ligands having the general formula:

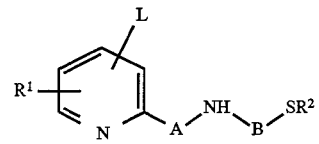

wherein $R^1$ is selected from the group consisting of hydrogen, alkyl, hydroxyl, alkoxyl, hydroxyalkyl, alkoxyalkyl, alkoxycarbonyl, or carbamoyl, wherein the carbon containing portion of such group contains 1 to 10 carbon atoms; $R^2$ is a suitable sulfur protecting group selected from the group consisting of acetyl, benzoyl, methoxyacetyl, 1–3-dioxacyclohexyl, 1,3-dioxacyclopentyl, alkoxycarbonyl, carbamoyl, alkoxyalkyl, dialkoxyalkyl, tetrahydropyranyl, tetrahydrofuranyl, p-methoxybenzyl, benzhydryl, trityl, and the like; L is selected from the group consisting of

or

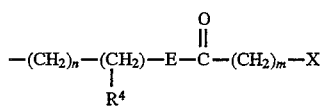

wherein k, l, m and n are 0 to 10, preferably 1 to 6; E is —O—, —S—, or —NR$^3$, wherein $R^3$ and $R^4$ are defined in the same manner as $R^1$ above, and wherein X is a suitable coupling moiety selected from the group consisting of formyl, carboxyl, hydroxyl, amino, t-butoxycarbonylamino, chloro-carbonyl, N-alkoxycarbamoyl, succinimidoloxycarbonyl, imidate, isocyanate, isothiocyanate, tetrafluorophenoxy, and the like; A is selected from the group consisting of

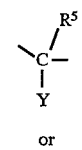

or

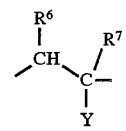

wherein $R^5$ to $R^7$ are defined in the same manner as $R^1$ above, and wherein Y is defined in the same manner as L above; and B is selected from the group consisting of

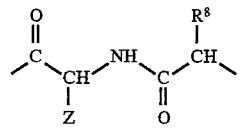

or

-continued

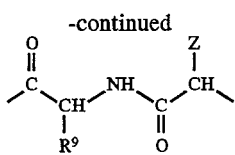

wherein $R^8$ and $R^9$ are defined in the same manner as $R^1$ above, and wherein Z is defined in the same manner as L above.

In a preferred embodiment, ligands according to the present invention have the general Formula (I) above, wherein A is

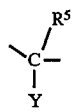

wherein $R^5$ and Y are hydrogens; B is

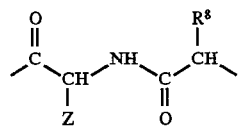

wherein $R^8$ is hydrogen and Z is

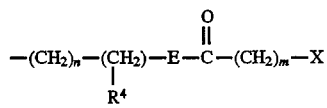

wherein $R^4$ is hydrogen, E is an —NH— group, m is 2, n is 3, and X is carboxyl; $R^2$ is a benzoyl or a tetrahydropyranyl group; and L is hydrogen.

In another preferred embodiment, ligands according to the present invention have the general Formula (I) wherein A is

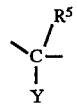

wherein $R^5$ and Y are hydrogens; B is

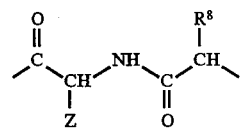

wherein $R^8$ is hydrogen and Z is —$(CH_2)_k$—X wherein k is 2 or 4, and X is one of an amino, a carboxyl or a hydroxyl; $R^2$ is a benzoyl or a tetrahydropyranyl group; and L is hydrogen.

The novel ligands described above may be incorporated into radionuclide complexes used as radiographic imaging agents. Further, these ligands or complexes can be covalently or non-covalently attached to biologically active carrier molecules, such as, antibodies, enzymes, peptides peptidomimetics, hormones, and the like. The complexes of the present invention are prepared by reacting one of the aforementioned ligands with a radionuclide containing solution under radionuclide complex forming reaction conditions. In particular, if a technetium agent is desired, the reaction is carried out with a pertechnetate solution under technetium 99 m complex forming reaction conditions. The solvent may then be removed by any appropriate means, such as evaporation. The complexes are then prepared for administration to the patient by dissolution or suspension in a pharmaceutically acceptable vehicle.

The ligands of the present invention may be prepared from commercially available starting materials such as 2-(2-aminoethyl) pyridine, 2-aminomethyl pyridine, lysine, glutamic acid, aminoadipic acid, mercaptoacetic acid, etc. by standard synthetic methods as described in the Examples.

Radionuclide complexes of the above-described ligand may have the general formula:

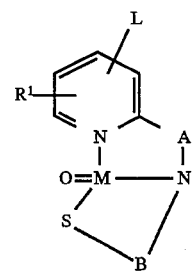

wherein M represents an appropriate radionuclide, such as technetium or rhenium and wherein $R^1$, L, A and B are as defined above in Formula (I).

In a preferred embodiment, a technetium radionuclide complex having the general Formula (II) may be formed from a pertechnetate solution and a ligand having the general Formula (I) above, wherein $R^1$ and L are hydrogens; A is

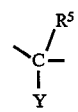

wherein $R^5$ and Y are hydrogens; and B is

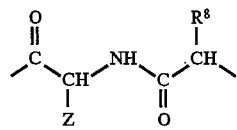

wherein $R^8$ is hydrogen and Z is

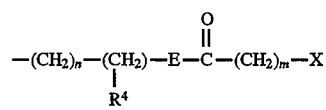

wherein R4 is hydrogen, E is an —NH— group, m is 2, n is 3, and X is carboxyl.

In another preferred embodiment, a technetium complex having the general Formula (II) may be formed from a pertechnetate solution and a ligand having the general Formula (I) above, wherein $R^1$ and L are hydrogens; A is

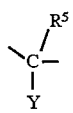

wherein $R^5$ and Y are hydrogens; and B is

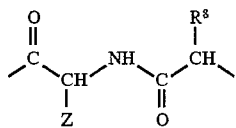

wherein $R^8$ is hydrogen and Z is $-(CH_2)_k-X$ wherein k is 2 or 4, and X is one of an amino, a carboxyl or a hydroxyl.

The radionuclide containing solution may be obtained from radionuclide generators in a known manner. For example, when forming a technetium complex, the pertechnetate solution may be obtained from a technetium generator in a known manner. The radionuclide complex forming reaction is then carried out under appropriate reaction conditions. For example, the technetium 99 m complex forming reaction is carried out under technetium complex forming temperatures, e.g. 20° C. to 100° C. for 10 minutes to several hours. The pertechnetate is used in technetium complex forming amounts, e.g. about $10^{-6}$ to $10^{-2}$ molar amounts.

The present invention also relates to imaging agents containing a radionuclide complex as described above, in an amount sufficient for imaging, together with a pharmaceutically acceptable radiological vehicle. The radiological vehicle should be suitable for injection or aspiration, such as human serum albumin; aqueous buffer solutions, e.g tris (hydromethyl) aminomethane (and its salts), phosphate, citrate, bicarbonate, etc; sterile water; physiological saline; and balanced ionic solutions containing chloride and or dicarbonate salts or normal blood plasma cations such as $Ca^{+2}$, $Na^+$, $K^+$, and $Mg^{+2}$.

The concentration of the imaging agent according to the present invention in the radiological vehicle should be sufficient to provide satisfactory imaging, for example, when using an aqueous solution, the dosage is about 1.0 to 50 millicuries. The imaging agent should be administered so as to remain in the patient for about 1 to 3 hours, although both longer and shorter time periods are acceptable. Therefore, convenient ampules containing 1 to 10 mL of aqueous solution may be prepared.

Imaging may be carried out in the normal manner, for example by injecting a sufficient amount of the imaging composition to provide adequate imaging and then scanning with a suitable machine, such as a gamma camera.

The present invention relates, in another significant aspect, to novel aminothiol ligands that are suitable for complexing with a radionuclide, and are useful as general imaging agents for diagnostic purposes. In particular, the present invention relates to novel ligands having the general formula:

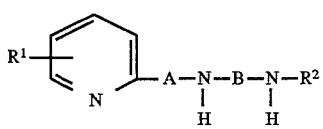

(III)

wherein $R^1$ and $R^2$ may be the same or different and are selected from the group consisting of hydrogen, alkyl, aryl, hydroxyl, alkoxyl, mono- or poly- hydroxyalkyl, mono- or poly- alkoxyalkyl, acyl, alkoxycarbonyl, or carbamoyl; A is selected from the group consisting of

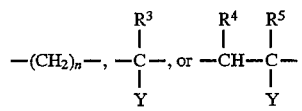

wherein n is 1 to 3, wherein $R^3$, $R^4$ and $R^5$ are defined in the same manner as $R^1$ and $R^2$ above, and wherein Y is

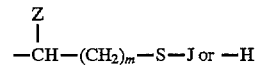

wherein m is 1 to 3, wherein Z is selected from the Group consisting of

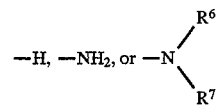

wherein $R^6$ and $R^7$ are defined in the same manner as $R^1$ and $R^2$ above, and wherein J is hydrogen or another suitable protecting group such as ethylaminocarbonyl; and B is selected from the group consisting of

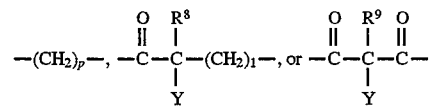

wherein p is 1 to 3, wherein 1 is 0 or 1, wherein $R^8$ and $R^9$ are defined in the same manner as $R^1$ and $R^2$ above, and wherein Y is as defined above.

In a preferred embodiment, ligands according to the present invention have the general formula (III) above, wherein $R^1$ is hydrogen; $R^2$ is selected from the group consisting of butoxycarbonyl, acetyl, ethyl, or hydrogen; A is $-(CH_2)_n-$ wherein n=2; and B is

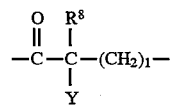

wherein 1=0, $R^8$ is hydrogen and Y is

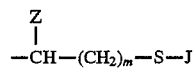

wherein m=1, Z is —H, and J is a suitable protecting group.

The present invention also relates to novel ligands having the general formula:

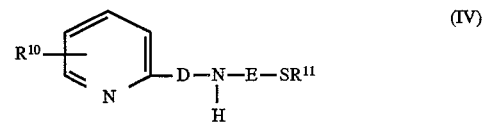

(IV)

wherein $R^{10}$ is selected from the group consisting of hydrogen, alkyl, aryl, hydroxyl, alkoxyl, mono- or poly- hydroxyalkyl, mono- or poly- alkoxyalkyl, acyl, alkoxycarbonyl, or carbamoyl; $R^{11}$ is a suitable sulfur protecting group selected from the group defined in the same manner as $R^{10}$ above; D is selected from the group consisting of

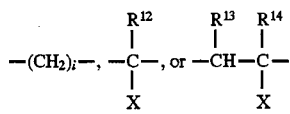

wherein i is 1 to 3, wherein $R^{12}$, $R^{13}$ and $R^{14}$ are defined in the same manner as $R^{10}$ above, and wherein X is

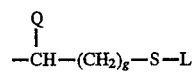

wherein g is 1 to 3, wherein Q is selected from the group consisting of

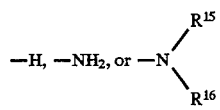

wherein $R^{15}$ and $R^{16}$ are defined in the same manner as $R^{10}$ above, and wherein L is hydrogen or another suitable protecting group such as ethylaminocarbonyl; and E is selected from the group consisting of

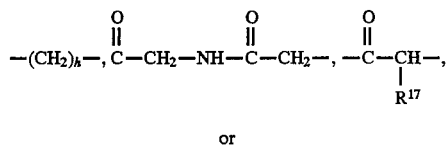

or

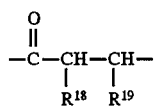

wherein h is 1 to 3, wherein $R^{17}$, $R^{18}$ and $R^{19}$ are defined in the same manner as $R^{10}$ above.

In another preferred embodiment, ligands according to the present invention have the general formula (IV) above, wherein $R^{10}$ is hydrogen; $R^{11}$ is

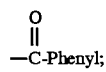

D is $-(CH_2)_i-$ wherein i=1; and E is

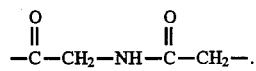

The novel ligands described above, may be incorporated into radionuclide complexes used as radiographic imaging agents. The complexes of the present invention are prepared by reacting one of the aforementioned ligands with a radionuclide containing solution under radionuclide complex forming reaction conditions. In particular, if a technetium agent is desired, the reaction is carried out with a pertechnetate solution under technetium 99 m complex forming reaction conditions. The solvent may then be removed by any appropriate means, such as evaporation. The complexes are then prepared for administration to the patient by dissolution or suspension in a pharmaceutically acceptable vehicle.

The ligands of the present invention may be prepared from commercially available starting materials such as 2-(2-aminoethyl)pyridine, 2-aminomethyl pyridine, homocysteinethiolactone, etc. by standard synthetic methods as described in the Examples.

Radionuclide complexes formed from the above-described ligands may have the general formula:

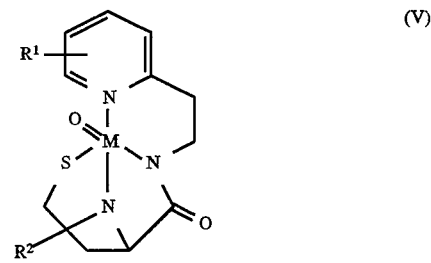

(V)

wherein M is an appropriate radionuclide such as technetium or rhenium, and $R^1$ and $R^2$ are as defined above in formula (III). In a preferred embodiment a technetium radionuclide complex having the general formula (V) may be formed from a pertechnetate solution and a ligand having the general formula (III) above, wherein $R^1$ is hydrogen; $R^2$ is butoxycarbonyl, acetyl, ethyl or hydrogen; A is $-(CH_2)_n-$ wherein n=2; and B is

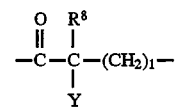

wherein l=0, $R^8$ is hydrogen and Y is

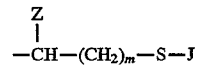

wherein m=1, Z is —H, and J is a suitable protecting Group.

Also, radionuclide complexes according to the present invention may have the general formula:

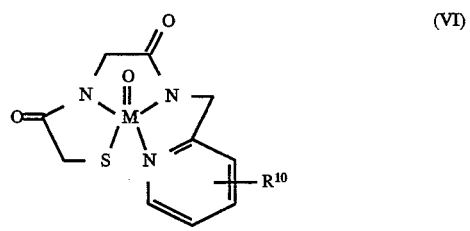

(VI)

wherein M represents an appropriate radionuclide, such as technetium or rhenium and wherein $R^{10}$ is as defined above in formula (IV). In a preferred embodiment, a technetium radionuclide complex having the general formula (VI) may be formed from a pertechnetate solution and a ligand having the general formula (IV) above, wherein $R^{10}$ is hydrogen; $R^{11}$ is

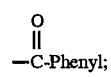

D is —(CH$_2$)$_i$— wherein i=1; and E is

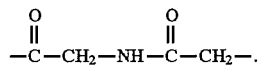

The radionuclide containing solution may be obtained from radionuclide generators in a known manner. For example, when forming a technetium complex, the pertechnetate solution may be obtained from a technetium generator in a known manner. The radionuclide complex forming reaction is then carried out under appropriate reaction conditions. For example, the technetium 99 m complex forming reaction is carried out under technetium complex forming temperatures, e.g. 20° C. to 100° C. for 10 minutes to several hours. A large excess of the appropriate ligands over the radionuclide complex forming amounts is preferably used. For example, when forming a technetium complex, at least a ten fold excess of the ligands over the pertechnetate solution is used. The pertechnetate is used in technetium complex forming amounts, e.g. about $10^6$ to $10^{12}$ molar amounts.

It is believed that certain radionuclide complexes of the present invention incorporating the ligands of the present invention have particular functional use as brain imaging agents. In particular, it is believed that these agents will act as opium alkaloid (e.g. morphine) mimics which may be selectively localized in the brain receptors, and may therefore exhibit optimal properties to function as diagnostic agents for the detection of brain disorders such as Alzheimer's disease, Parkinson's disease, narcotic addiction, etc.

A preferred complex for use in a brain imaging agent according to the present invention has the following formula:

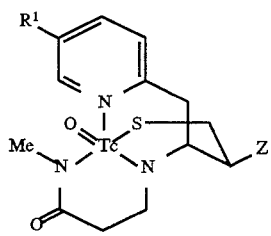

(VII)

wherein R$^1$ is as defined above in formula (III), and wherein Z is a primary, secondary or tertiary amino functionality. This complex may be formed by reaction of a pertechnetate solution with a ligand according to the present invention having the general formula (III) above, wherein R$^1$ is, in particular, hydrogen, hydroxyl, or methoxyl; R$^2$ is CH$_3$; A is

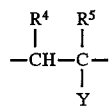

wherein R$^4$ and R$^5$ are hydrogen and Y is

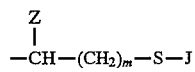

wherein m=1, Z is

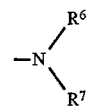

wherein R6 is hydrogen or CH$_3$ and R$^7$ is hydrogen or CH$_3$, and J is a suitable protecting group; and B is

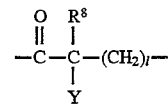

wherein l=1, R$^8$ is hydrogen and Y is —H.

A further preferred complex for use in a brain agent according to the present invention has the following formula:

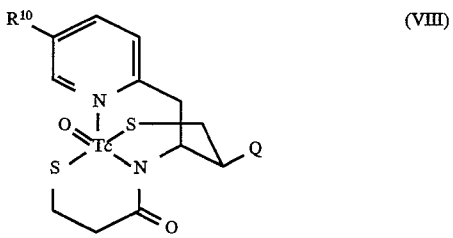

(VIII)

wherein R$^{10}$ is as defined above in formula (IV), and wherein Q is a primary, secondary or tertiary amino functionality. This complex may be formed by reaction of a pertechnetate solution with a ligand having the general formula (IV) above, wherein R$^{10}$ is, in particular, hydrogen, hydroxyl, or methoxyl; R$^{11}$ is hydrogen or another suitable protecting group; D is

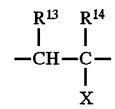

wherein R$^{13}$ and R$^{14}$ are hydrogen and X is

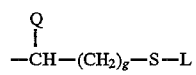

wherein g=1, Q is

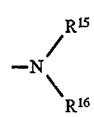

wherein R$^{15}$ is hydrogen or CH$_3$ and R$^{16}$ is hydrogen or CH$_3$, and L is a suitable protecting group; and E is

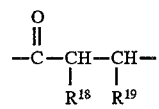

wherein R$^{18}$ and R$^{19}$ are hydrogen.

The present invention also relates to imaging agents containing a radionuclide complex as described above, in an amount sufficient for imaging, together with a pharmaceutically acceptable radiological vehicle. The radiological vehicle should be suitable for injection or aspiration, such as human serum albumin; aqueous buffer solutions, e.g tris (hydromethyl) aminomethane (and its salts), phosphate, citrate, bicarbonate, etc; sterile water; physiological saline; and balanced ionic solutions containing chloride and or dicarbonate salts or normal blood plasma cations such as $Ca^{+2}$, $Na^+$, $K^+$, and $Mg^{+2}$.

The concentration of the imaging agent according to the present invention in the radiological vehicle should be sufficient to provide satisfactory imaging, for example, when using an aqueous solution, the dosage is about 1.0 to 50 millicuries. The imaging agent should be administered so as to remain in the patient for about 1 to 3 hours, although both longer and shorter time periods are acceptable. Therefore, convenient ampules containing 1 to 10 ml of aqueous solution may be prepared.

Imaging may be carried out in the normal manner, for example by injecting a sufficient amount of the imaging composition to provide adequate imaging and then scanning with a suitable machine, such as a gamma camera.

In a further significant aspect of the present invention, novel $N_3S$ amide-thiolate ligands are disclosed. These ligands are distinguished from conventional amide-thiolate ligands by having an amine group in the $N_3S$ core which is rapidly converted to an amide upon complexation. The presence of the amine enhances the initial kinetics of chelate formation while the presence of the final amide provides a more a thermodynamically stable triamide-thiolate complex. Overall, the metal chelate formation kinetics are enhanced.

The "amine group" is preferably part of a pyridine ring containing a lower alkoxyl substituent in the 2 or 4 position. O -dealkylation occurs upon complexation which causes the amine to become a vinylogous amide. Thus, the amine is a masked amide. In the claimed compounds, the amide necessary to form the chelate is masked as an amine by the presence of 2 or 4 alkoxyl substituent in the pyridine ring. Upon initial complex formation, O-dealkylation occurs to regenerate the amide.

The following Generalized structure illustrates a typical $N_3S$ ligands containing a masked amide group within the scope of the present invention.

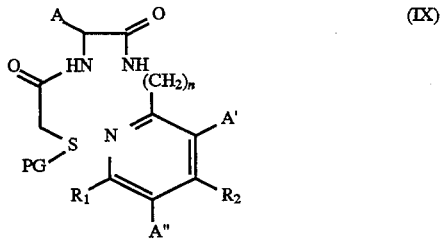

(IX)

Where A is an H, alkyl, a functionalized substituent of an α-amino acid, or —$(CH_2)_n$—X, where X is a functional group for coupling the ligand to a biomolecule, n' is from 1 to 10; $R_1$ or $R_2$ is a lower alkoxyl group, preferably methyoxyl, and the remaining $R_1$ or $R_2$ is H, alkyl, electron withdrawing group, or optionally —$(CH_2)_n$—X if A is not —$(CH_2)_n$—X; A' or A" is H, alkyl, electron withdrawing group, or optionally —$(CH_2)_n$—X if A, $R_1$, $R_2$ is not —$(CH_2)_n$—X; n is 1 or 2; and PG is a protecting group. Examples of possible functional groups for coupling the ligand to a biomolecule include carbonyl, active ester, isocyanate, isothiocyanate, imidate, maleimide or an activated electrophilic center such as C=C, halocarbonyl, halosulfonyl, and haloacetyl. Electron withdrawing groups, such as carboxylic acid, are well known to those skilled in the art and include functional groups containing unsaturation or electronegative atoms, such as halogen.

The protecting group prevents potential oxidation of the sulfur and prevents the sulfur from reacting with other reactive groups in the biologically active molecule during attachment of the ligand. The protecting group remains stable during kit formulation and stable until the metal (radioisotope) is added by the end user for conversion to the chelate. The protecting groups are removed concomitantly during complex formation, i.e., the protecting groups are removed only under labeling conditions and in the presence of the metal. Examples of typical protecting groups known in the art include hemithioacetal groups such as ethoxyethyl, methoxymethyl, substituted and unsubstituted tetrahydrofuranyl and tetrahydropyranyl, acetamidoalkyl such as actetamidomethyl, S-acyl such as S-alkanoyl, S-benzoyl, and S-substituted benzoyl groups.

The following examples are offered to further illustrate the preparation of ligands and radionuclide complexes within the scope of the present invention. These examples are intended to be purely exemplary and should not be viewed as a limitation on any claimed embodiment.

EXAMPLE 1

Preparation of 2-aza-4-[N-(S-benzoyl) mercaptoacetyl-8-[N-(t-butoxy)carbonyl]amino-3-oxo-1-(2-pyridyl)octane A mixture of 4-amino-2-aza-8-[N-(t-butoxy)carbonyl]-amino-3-oxo-1-(2-pyridyl)octane (1.70 g, 5 mmol) and N-[(S-benzoyl) mercapto]acetoxy-succinimide (1.53 g, 5.5 mmol) in acetonitrile (15 mL) was stirred at ambient temperature for 4 hours. The reaction mixture was poured onto water (100 mL) and kept at 4° to 8° C. (refrigerator) for about 16 hours. The precipitate was collected by filtration, washed well with water, dried, and recrystallized from acetonitrile to give 1.2 g of colorless solid, mp 133°–135° C. Anal. Calcd. for $C_{25}H_{34}N_4O_5S$: C, 60.70; H, 6.61; N, 10.89; S, 6.26. Found: C, 60.79; H, 6.65; N, 10.91; S, 6.30.

EXAMPLE 2

Preparation of 2-aza-4-[N-(S-tetrahydropyranyl)-mercapto]acetyl-8-N-(t-butoxy)carbonyl]amino-3-oxo-1-(2-pyridyl) octane A mixture of 4-amino-2-aza-8-[N-(t-butoxy)carbonyl)] amino-3-oxo-1-(2-pyridyl)octane (3.36 g, 10 mmol) and N-[(S-tetrahydropyranyl)mercapto-acetoxy]-succinimide (2.40 g, 10 mmol) in acetonitrile (25 mL) was stirred at ambient temperature for 4 hours. The reaction mixture was poured onto water (100 mL) and extracted with methylene chloride (3×25mL). The combined organic extracts were washed with water, dried ($MgSO_4$), filtered, and the filtrate taken to dryness under reduced pressure. The gummy residue was chromatographed over silica gel (200 g) using chloroform/methanol (95:5) as eluent to give 3.2 g of off-white solid, mp 87°–90° C. 13C—NMR ($CDCl_3$)δ171.8, 171.7, 170.0, 156.9, 156.7, 156.3, 149.3, 137.0, 122.5, 121.9, 84.0, 83.6, 79.0, 66.2, 65.7, 53.2, 44.4, 44.3, 40.0, 35.0, 34.6, 31.7, 31.0, 29.4, 28.2, 25.0, 24.9, 22.4, 21.9, 21.6.

EXAMPLE 3

Preparation of 6-aza-4-[N-(S-benzoyl)mercapto] acetyl-5-oxo-7-(2-pyridyl)-heptanoic acid A mixture of t-butyl 6-aza-4-[N-(S-benzoyl)-mercapto] acetyl-5-oxo-7-(2-pyridyl)heptanoate (2.35 g, 5mmol) and trifluoroacetic acid (5 mL) was kept at ambient temperature for 1 hour. The solution was then poured onto ether (100 mL). The precipitate was then collected by filtration, washed well with ether, and dried to yield 1.5 g of off white solid. $^1$H—NMR (DMSO-d$_6$) δ8.49–8.71 (m, 3H), 7.85–8.00 (m, 3H), 7.60–7.70 (m, 1H), 7.40–7.60 (m, 4H), 4.45 (d, 2H), 4.31 (m, 1H), 3.87 (dd, 2H), 2.27 (m, 2H), 1.95 (m, 1H), 1.80 (m, 1H). $^{13}$C—NMR (DMSO-d$_6$) δ191.1, 174.4, 172.0, 167.7, 157.5, 146.7, 140.3, 136.3, 134.5, 129.5, 127.2, 123.5, 122.5, 52.7, 42.9, 32.6, 30.1, 27.0. FAB mass spectrum, m/Z 416 (M+1).

EXAMPLE 4

Preparation of 7-aza-5-N-[(5-benzoyl)mercapto] acetyl-1-N-(t-butoxy-carbonyl) amino-6-oxo-9-(2-pyridyl)nonane A mixture of N-t-BOC-lysine-2-(2-pyridyl)ethylamide (1.75 g, 5 mmol) and N-[(5-benzoyl)mercapto]acetoxy-succinimide (1.53 g, 5.5 mmol) in acetonitrile (15 mL) was stirred at ambient temperature for four hours. The reaction mixture was poured onto water (100 ml) and cooled in ice-salt bath for two hours. The precipitate was collected by filtration, washed with water, dried, and recrystallized from acetonitrile to give 2.3 g (88%) of colorless solid. m.p. 138°–140° C. Anal. Calcd. for C$_{26}$H$_{36}$N$_4$O$_5$S: C, 61.36; H, 7.27; N, 10.67; S, 6.10. Found: C, 61.39; H, 7.18; N, 10.62; S, 6.01.

EXAMPLE 5

Preparation of technetium-99 m complex of the ligand in Example 1

A solution of the ligand in Example 1 (130 μL of 0.8 mg/mL stock solution in isopropyl alcohol) was incubated for 10 minutes at pH 12 (25 μL of 0.5M sodium phosphate). The mixture was then transferred to a vial containing stannous chloride solution (25 μL of 4 mg/mL stock solution in 0.05N HCl) and sodium pertechnetate solution (1 mL, 4 mCi/mL). The entire mixture was heated in boiling water bath for 5 minutes. The product was isolated and purified by reverse phase HPLC to give neutral $^{99m}$Tc (V) complex in about 50% yield.

EXAMPLE 6

Preparation of technetium-99 m complex of the ligand in Example 2

To a mixture of sodium gluconate (50 mg) and stannous chloride (1.2 mg) in water (1 mL) was added sodium pertechnetate (1 mL, 4 mCi/mL), 0.1N HCl (5 μL), and the ligand in Example 2 (115 μL of 1 mg/mL stock solution in isopropyl alcohol). The entire mixture was heated in boiling water bath for 5 minutes. The product was isolated and purified by reverse phase HPLC to give neutral $^{99m}$Tc (V) complex in about 75% yield.

EXAMPLE 7

Preparation of 10-[(S-tetrahydropyranyl)mercapto]-acetamido-5,12-diaza-4,11-dioxo-13(2-pyridyl) tridecanoic acid A mixture of 4-(4-amino)butyl-3,6-diaza-2,5-dioxo-1-(S-tetrahydropyranyl)mercapto-7-(2-pyridyl)heptane (790 mg, 2.0 mmol) and S-tetrahydropyranylmercaptoacetic acid (220 mg, 2.2 mmol) in acetonitrile (10mL) was heated under reflux for four hours and stirred at ambient temperature for sixteen hours. The solvent was removed under reduced pressure and the residue was purified by flash chromatography over reverse phase (25 g) eluted with water followed by methanol/water (1:1). Evaporation of the solvent afforded the desired ligand (510 mg) as colorless, amorphous solid. Anal. Calcd. for C$_{23}$H$_{34}$N$_4$O$_6$S ×0.33 H$_2$O: C, 55.20; H, 6.93; N, 11.20; S, 6.40: H$_2$O, 1.20 Found: C, 54.81; H, 6.99; N, 11.18; S, 6.39: H$_2$O, 1.19. Mass spectrum (thermospray) M/Z 495 (M+1).

The choice of protecting groups for the ligands according to the present invention has been found to be important. In particular, finding the proper protecting group for protection of the sulfur moiety has created difficulty in past ligand technology. It has been discovered that the use of hemithioacetal protecting groups such as tetrahydropyrannyl (THP) are especially useful during the labelling procedures.

Labelling of pyridine ligands as described above having a hemithioacetal protecting group has been carried out as shown in the following examples.

EXAMPLE 8

Preparations were made as follows:

To 0.1 mL stannous gluconate (from a lyophilized kit containing 50 mg sodium gluconate and 1.2 mg stannous chloride, and reconstituted with 1.0mL of degassed water) was added 1.0 mL pertechnetate, Tc-99 m (about 3 mCi). The above is allowed to stand for 5 min at room temperature, before it is adjusted for pH with either HCl or NaOH (target Ph were 5, 6, 7 and 8). 0.12 mL of a pyridine ligand (SN$_2$Py) (0.88 mg/mL, 33% IPA/water) was then added. The preparations were incubated in a boiling water bath for 5 minutes.

An aliquot of the preparation was injected on an HPLC (C18 reverse phase), and the results of the radioactive profiles were integrated. Radiolabelling yields (RCY) are expressed as a percent of the peak of interest (Tc-99 m SN$_2$Py). Recovery studies were performed by measuring the amount of activity injected on the system vs recovered. The pH of the preparations were also measured with a pH electrode.

Example 8: Results

| Target pH | RCY | Recovery (%) | Measured pH |
|---|---|---|---|
| 5 | 43.1 | 90 | 5.1 |
| 6 | 53.6 | ND | 6.0 |
| 7 | 89.9 | 84 | 7.6 |
| 8 | 86.7 | 91 | 8.8 |

EXAMPLE 9

Three preparations were done following the same protocol set forth in Example 8, except that dilute Tc-99 pertechnetate was added to the Tc-99 m in order to carry more Tc mass.

One preparation was a control (prep pH 7) and the two other preparations contained an additional 5 nanomoles of Tc-99 (since 1 mL TcO$_4^-$ is used, the preparation would be made with 5 μM Tc, the highest usually eluted from a Mo-99/Tc-99 m generator). Among these preparations, one was done at 50° C. for 30 min instead of the 100° C. (boiling water bath) for 5 min.

Example 9: Results

| Preparation    | RCY  | Recovery (%) | Measured pH |
|----------------|------|--------------|-------------|
| control        | 89.9 | 89           | 7.3         |
| 100° C., 5 min | 70.2 | 83           | 7.6         |
| 50° C., 30 min | 25.4 | 79           | ND          |

The results above clearly indicate that pyridine ligands having a THP protecting group can be labelled in a wide range of pH conditions ranging from acidic to basic. The preparations made with additional Tc-99 showed somewhat reduced kinetics but still provided good yield of product. This precludes the possibility that the results could be explained by radiolabelling of an impurity of the ligand. Radiolabelling was shown to occur even at reduced temperature.

Based on the above results, it is believed that the pyridine ligand plays a major role in the radiolabelling properties. In addition, it is believed that the THP protecting group, previously thought to be an acid cleavable protector can be used to protect the ligand and allow excellent radiolabelling of the product, even under neutral and basic conditions.

EXAMPLE 10

Preparation of 5-aza-3-(N-t-butoxycarbonyl)amino-1-mercapto-4-oxo-7-(2-pyridyl)-heptane

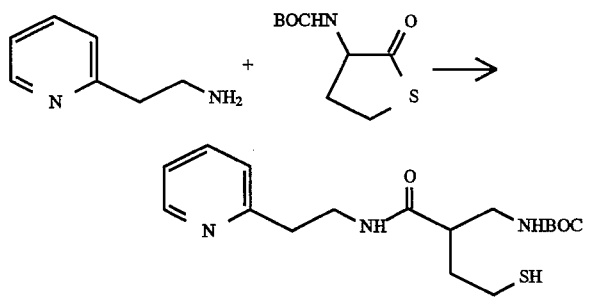

A mixture of 2-(2-aminoethyl)pyridine (2.44 g, 0.02 mol) and N-t butoxycarbonyl-homocysteinethiolactone (4.22 g, 0.02 mol) in acetonitrile (50 ml) was heated under reflux for 12 hours. Thereafter, the reaction mixture was kept at room temperature for 6 hours by which time colorless crystals had separated. The solid was collected by filtration, washed with cold acetonitrile, and dried. $^{13}$C—NMR (CDCl$_3$) δ171.2, 159.3, 155.4, 149.2, 136.4, 123.3, 121.5, 79.9, 53.7, 38.8, 36.9, 34.8, 32.6, 28.3.

EXAMPLE 11

Preparation of 3-acetamido-5-aza-1-mercapto-4-oxo-7-(2-pyridyl) heptane

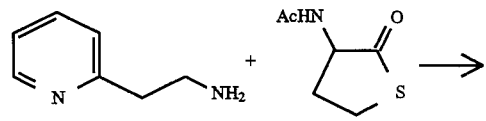

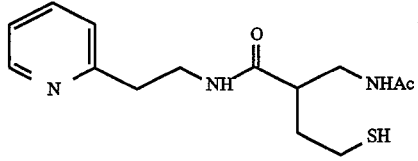

A mixture of N-acetylhomocysteinethiolactone (4.77 g, 0.03 mol) and 2-(2-aminoethyl) pyridine (3.66 g, 0.03 mol) in acetonitrile (50 ml) was heated under reflux for 12 hours. The solvent was removed under reduced pressure and the residue was treated with ethyl acetate (50 ml). The precipitate was collected, dried and recrystallized from acetonitrile to give colorless solid. $^{13}$C—NMR (CDCl$_3$) δ1 171.4, 170.6, 159.4, 149.3, 136.6, 123.4, 121.8, 51.7, 38.5, 36.8, 34.9, 32.7, 22.8.

EXAMPLE 12

Preparation of 3-amino-5-aza-1-mercapto-4-oxo-7-(2-pyridyl) heptane

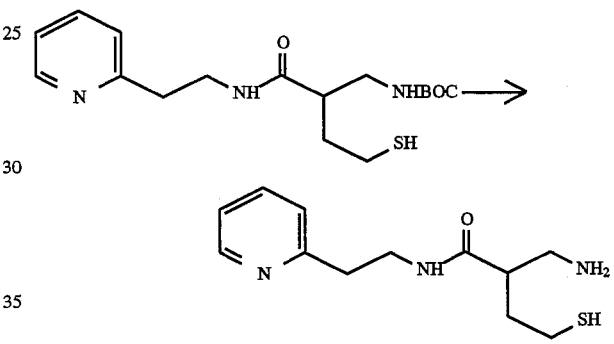

A solution of the butoxycarbonyl derivative from Example 10, (4 g) and trifluoroacetic acid (20 ml) was kept at room temperature for 1 hour. The reaction mixture was poured onto ether (500 ml). The precipitate was collected, washed with ether and dried. The compound was pure enough for the next step.

EXAMPLE 13

Preparation of 5-aza-3-ethylamino-1-mercapto-4-oxo-7-(2-pyridyl) heptane

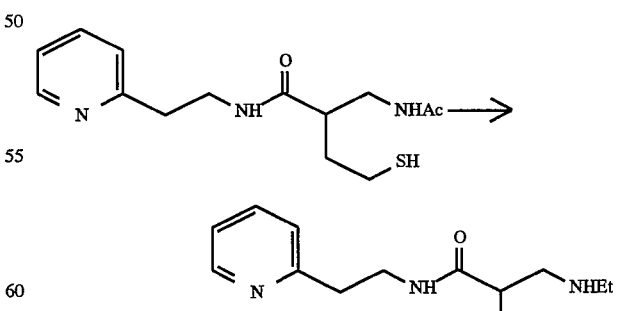

A solution of diborane in tetrahydrofuran (1M, Aldrich) (60 ml) was added dropwise to an ice-cold solution of the diamide of Example 2 (4 g) in tetrahydrofuran (20 ml). After the addition, the reaction mixture was heated under reflux for 2 hours. The reaction mixture was then cooled in an ice bath and excess diborane was decomposed by dropwise addition of ice-cold water. The solution was taken to dryness under reduced pressure and the residue was redissolved in methylene chloride (100 ml) washed with water (2×100 ml), dried (Na$_2$SO$_4$), filtered and the filtrate was taken to dryness under reduced pressure. The residue was chromatographed over silica gel (200 g) using CH$_2$Cl$_2$/CH$_3$OH (9:1) as eluent to furnish the desired compound as colorless gum (1 g). $^{13}$C—NMR (CDCl$_3$) δ174.7, 159.0, 148.9, 137.2, 123.7, 121.9, 61.2, 49.8, 42.3, 38.3, 37.4, 36.8, 20.8, 14.7.

EXAMPLE 14

Preparation of 7-(S-benzoyl) mercapto-2,5-diaza-3,6-dioxo-1-(2-pyridyl) heptane

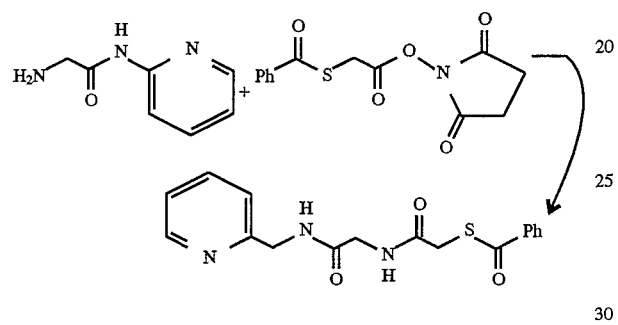

A mixture of S-(benzoyl)mercaptoacetoxy succinimide (1.4 g) and 1-amino-3-aza-2-oxo-4-(2-pyridyl) butane (0.8 g) in acetonitrile (20 ml) was stirred at room temperature for 1 hour. The white precipitate was collected, washed with water, dried, and recrystallized from acetonitrile to give 700 mg of colorless solid. $^{13}$C—NMR (CDCl$_3$) δ191.9, 168.9, 156.5, 149.2, 137.0, 136.1, 134.3, 128.9, 127.7, 122.5, 122.0, 44.3, 43.3, 32.5.

EXAMPLE 15

$^{99m}$Tc labelling of the ligand of Example 10

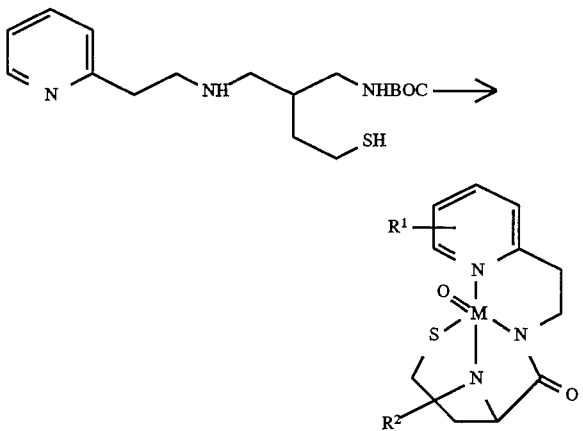

A mixture of the ligand produced in Example 10 (10 mg) in ethanol (0.9 ml) was treated with 0.01N NaOH (0.1 ml) and technetium tartarate solution (0.1 ml). The entire mixture was heated at 100° C. for 30 minutes. After cooling, the neutral complex was purified by reverse phase HPLC.

EXAMPLE 16

$^{99m}$Tc labelling of the ligand of Example 14

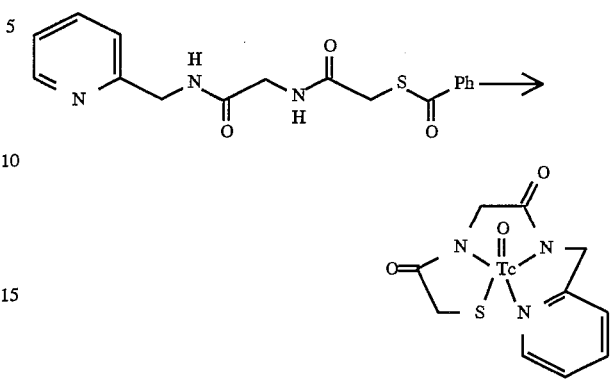

A mixture of the ligand produced in Example 14 (10 mg) in ethanol (0.1 ml) and 0.0001N NaOH (0.9 ml) and technetium tartarate solution (0.1 ml) was heated at 100° C. for 45 minutes to yield neutral complex in high yield and purity. No HPLC purification was required.

EXAMPLE 17

Preparation of 5-aza-3-(N-t-butoxycarbonyl)amino-1-S-[(N-ethyl)carbamoyl]mercapto-4-oxo-7-(2-pyridyl)-heptane

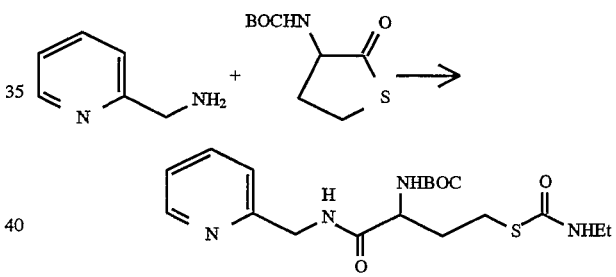

A mixture of 2-aminomethyl pyridine (2.44 g, 0.02 mol) and N-t butoxycarbonyl-homocysteinethiolactone (4.22 g, 0.02 mol) in acetonitrile (50 ml) was heated under reflux for 16 hours. Thereafter, the reaction mixture was cooled to room temperature and was treated with ethyl isocyanate (2 ml). The solution was stirred at room temperature for 16 hours. The solvent was removed under reduced pressure and the residue was treated with CH$_2$Cl$_2$ (50 ml) and water (50ml). The organic layer was separated, washed with water, dried (MgSO$_4$), filtered, and the filtrate taken to dryness under reduced pressure to give the desired compound as a pale yellow gum. Purification by silica gel chromatography (ethyl acetate acetone, 4:1) yielded pure ligand (1.2 g) as an off white solid. $^{13}$C—NMR (CDCl$_3$) δ171.6, 156.6, 155.6, 149.0, 136.7, 122.3, 121.7, 80.0, 53.7, 44.6, 36.4, 33.9, 28.3, 26.1, 14.9.

The following examples illustrate exemplary methods of preparing various pyridine derivatives which may be used to prepare ligands within the scope of the present invention.

EXAMPLE 18

The following diagram illustrates the synthesis of a pyridine derivative having a methoxyl substituent in the 2 position. Commercially available 2,6-dichloropyridine is converted to 2-cyano-6-methoxypyridine by successive nucleophilic substitution with cyanide and methoxide followed by catalytic reduction to give compound (A).

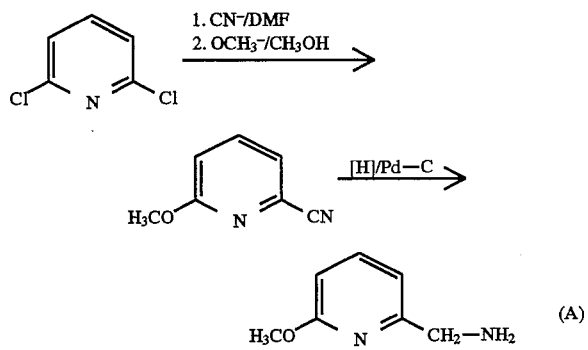

The final compound (A) may be used to prepare a ligand within the scope of the present invention in which n=1.

EXAMPLE 19

The following diagram illustrates the synthesis of a pyridine derivative having a methoxyl substituent in the 4 position. The initial 4-chloropyridine starting material is commercially available. The individual reactions are known to those skilled in the art.

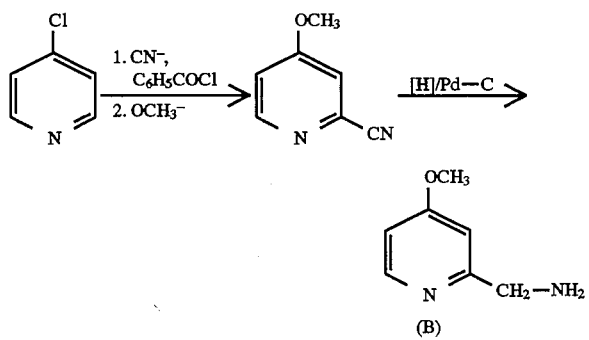

Support for the first step conversion of the chloro pyridine to the 2-cyano derivative is found in Yakugaku Zasshi, Vol. 65B, p. 582 (1945). The final compound (B) may be used to prepare a ligand within the scope of the present invention in which n=1.

EXAMPLE 20

The following diagram illustrates the synthesis of a pyridine derivative having a methoxyl substituent in the 2 position. Commercially available 2,6-dichloropyridine is converted to α-cyano-α-methylthio-6-methoxypyridine by successive nucleophilic substitution with the anion of methylthioacetonitrile and methoxide. Dethiation and reduction of the nitrile is accomplished with Ra—Ni in a single step to give compound (C).

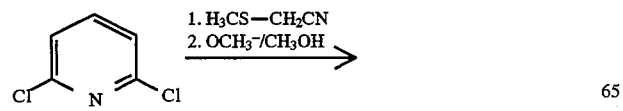

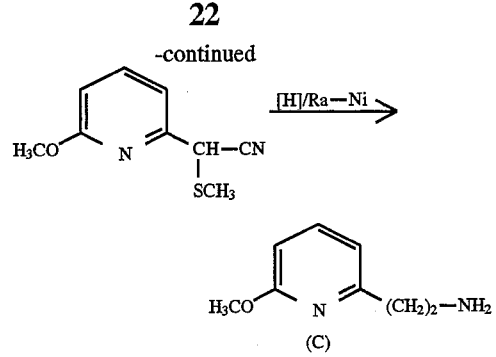

The final compound (C) may be used to prepare a ligand within the scope of the present invention in which n=2.

The following examples are offered to further illustrate the synthesis of potential triamide-thiolate ligands within the scope of the present invention.

EXAMPLE 21

In this example, compounds A (for n=1) or B (for n=2) are used as starting materials for the synthesis of ligands containing masked amides within the scope of the present invention. The other starting material, Z-glutamic acid γ-benzyl ester, is commercially available. The individual reactions are known to those skilled in the art.

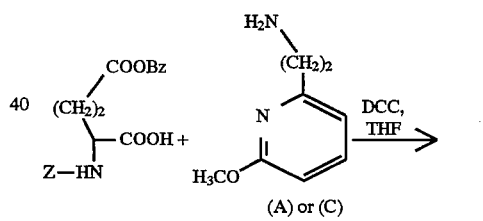

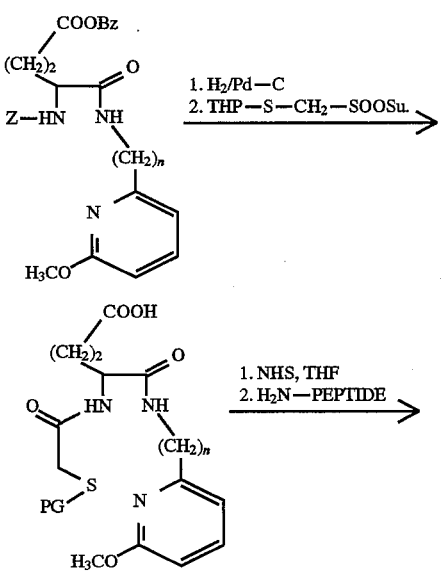

-continued

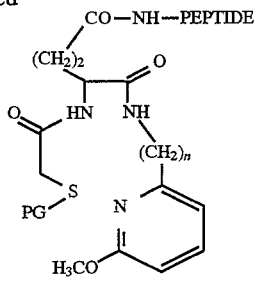

The same reaction conditions described above may be used when the alkoxyl group is in the 4 position (for compound B).

The quartenization of nitrogen heterocycles followed by O-dealkylation according to the Hilbert and Johnson reaction (alkoxyl group in the 2 position) reported in *J. Amer. Chem. Soc.*, Vol. 52, p. 2001 (1930) as shown below:

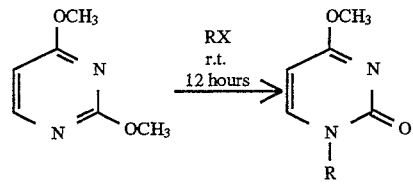

Where R is alkyl or acetal and X is a halide or anionic counter ion. Dealkylation of the alkoxyl group in the 4 position is reported by Fry et al., *J. Chem. Soc.* p. 5062 (1960) as shown below:

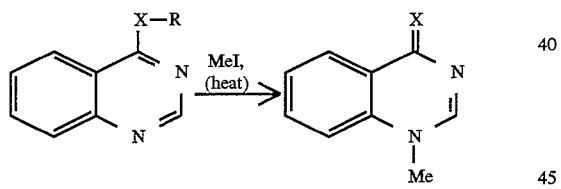

Where X is O or S, and when X is O, then R is phenyl and when X is S, then R is $CH_3$.

The ligands are labeled according to standard labeling techniques. The following diagram illustrates the O-dealkylation and formation of a vinylogous amide for ligands in which the alkoxyl substituent is in the 2 position.

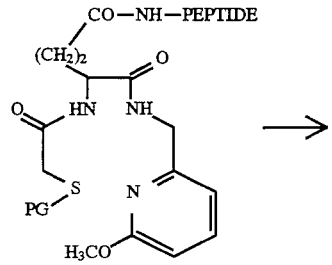

-continued

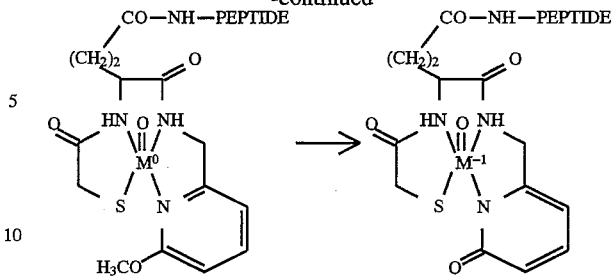

The following diagram illustrates the O-dealkylation and formation of a vinylogous amide for ligands in which the alkoxyl substituent is in the 4 position.

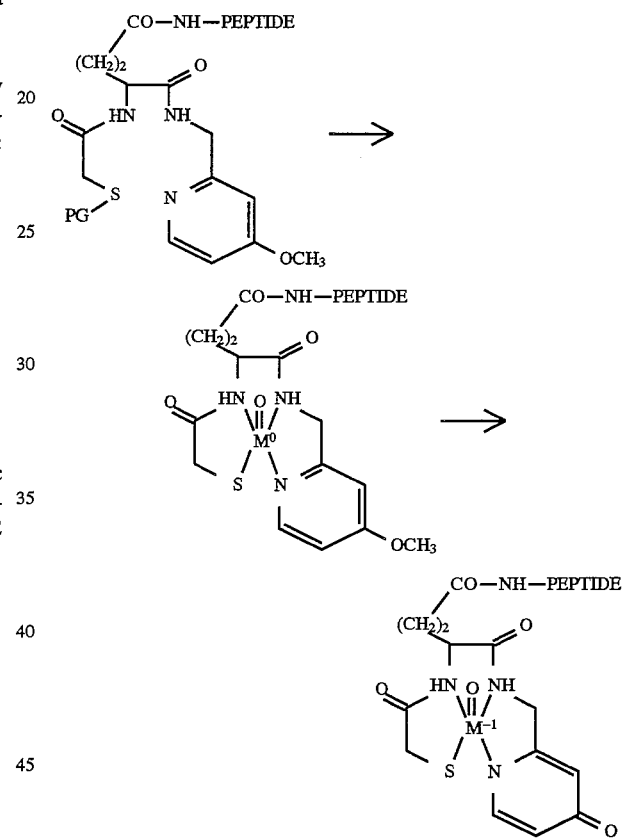

As described above, the amide-thiolate ligands within the scope of the present invention may be coupled to biomolecules according to standard procedures known in the art. The conjugated biomolecules are then labelled with suitable radionuclides and administered to a patient for diagnostic imaging or therapeutic use.

After the amide-thiolate ligands of the present invention are prepared and labelled according to the procedure described above, the compounds may be used with a pharmaceutically acceptable carrier in conventional diagnostic imaging procedures. In this procedure, a diagnostically effective quantity of the compound, for example in the form of an injectable liquid, is administered to a warm-blooded animal and then imaged using a suitable detector, e.g. a gamma camera. Images are obtained by recording emitted radiation of tissue or the pathological process in which the radioactive peptide has been incorporated, which in the present care of tumors, thereby imaging at least a portion of the body of the warm-blooded animal.

Pharmaceutically acceptable carriers for either diagnostic or therapeutic use include those that are suitable for injection or administration such as aqueous buffer solutions, e.g. tris(hydroxymethyl)aminomethane (and its salts), phosphate, citrate, bicarbonate, etc., sterile water for injection, physiological saline, and balanced ionic solutions containing chloride and/or bicarbonate salts of normal blood plasma cations such as $Ca^{+2}$, $Na^+$, $K^+$ and $Mg^{2+}$. Other buffer solutions are described in *Remington's Practice of Pharmacy*, 11th edition, for example on page 170. The carriers may contain a chelating agent, e.g. a small amount of ethylenediaminetetraacetic acid, calcium disodium salt, or other pharmaceutically acceptable chelating agents.

The concentration of labelled biomolecule and the pharmaceutically acceptable carrier, for example in an aqueous medium, varies with the particular field of use. A sufficient amount is present in the pharmaceutically acceptable carrier in the present invention when satisfactory visualization of the tumor is achievable or therapeutic results are achievable.

The inventions described herein may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within their scope.

What is claimed is:

1. A ligand useful in forming radionuclide complexes, said ligand having the general formula:

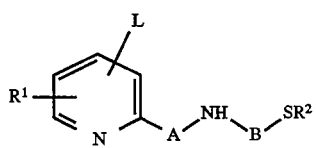

wherein $R^1$ is selected from the group consisting of hydrogen, alkyl, hydroxyl, alkoxyl, hydroxyalkyl, alkoxyalkyl, alkoxycarbonyl, or carbamoyl, wherein the carbon containing portion of such group contains 1 to 10 carbon atoms; $R^2$ is a suitable sulfur protecting group selected from the group consisting of acetyl, benzoyl, methoxyacetyl, 1-3-dioxacyclohexyl, 1,3-dioxacyclopentyl, alkoxycarbonyl, carbamoyl, alkoxyalkyl, dialkoxyalkyl, tetrahydropyranyl, tetrahydrofuranyl, p-methoxybenzyl, benzhydryl, and trityl, wherein the carbon containing portion of such group contains 1 to 10 carbon atoms; L is selected from the group consisting of

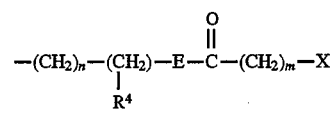

or

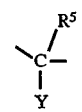

wherein k, l, m and n are 0 to 10; E is —O—, —S—, or —NR³, wherein $R^3$ and $R^4$ are defined in the same manner as $R^1$ above, and wherein X is a suitable coupling moiety selected from the group consisting of formyl, carboxyl, hydroxyl, amino, t-butoxycarbonylamino, chlorocarbonyl, N-alkoxycarbamoyl, succinimidoloxycarbonyl, imidate, isocyanate, isothiocyanate, and tetrafluorophenoxy; A is selected from the group consisting of

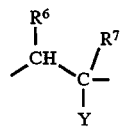

or

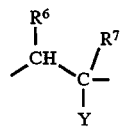

wherein $R^5$ to $R^7$ are defined in the same manner as $R^1$ above, and wherein Y is defined in the same manner as L above; and B is selected from the group consisting of

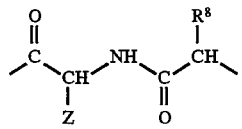

or

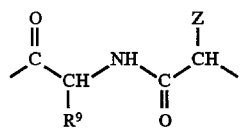

wherein $R^8$ and $R^9$ are defined in the same manner as $R^1$ above, and wherein Z is defined in the same manner as L above.

* * * * *